US012106480B2

(12) United States Patent
Chen et al.

(10) Patent No.: US 12,106,480 B2
(45) Date of Patent: *Oct. 1, 2024

(54) SYSTEMS AND METHODS FOR PROCESSING ELECTRONIC MEDICAL IMAGES TO DETERMINE ENHANCED ELECTRONIC MEDICAL IMAGES

(71) Applicant: Boston Scientific Scimed, Inc., Maple Grove, MN (US)

(72) Inventors: Longquan Chen, Andover, MA (US); Niraj P. Rauniyar, Plymouth, MN (US); Evan Gyllenhaal, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 194 days.

This patent is subject to a terminal disclaimer.

(21) Appl. No.: 17/804,610

(22) Filed: May 31, 2022

(65) Prior Publication Data

US 2022/0292682 A1 Sep. 15, 2022

Related U.S. Application Data

(63) Continuation of application No. 16/999,464, filed on Aug. 21, 2020, now Pat. No. 11,379,984.

(Continued)

(51) Int. Cl.
*G06T 7/00* (2017.01)
*A61B 18/26* (2006.01)
(Continued)

(52) U.S. Cl.
CPC .............. *G06T 7/0016* (2013.01); *G06T 5/00* (2013.01); *G06T 5/30* (2013.01); *A61B 18/26* (2013.01);
(Continued)

(58) Field of Classification Search
CPC ......... G06T 2207/10016; G06T 7/0016; G06T 7/292; G06T 2207/10068; G06T 5/001;
(Continued)

(56) References Cited

U.S. PATENT DOCUMENTS

2009/0297004 A1* 12/2009 Baumgart .............. G16H 20/17
382/130
2014/0112566 A1* 4/2014 Steinberg ............... A61B 34/10
382/131
(Continued)

FOREIGN PATENT DOCUMENTS

EP 3646335 B1 * 1/2023 ............. G06K 9/209
WO 2017149370 A1 9/2017
(Continued)

OTHER PUBLICATIONS

3-D Ultrasound Volume Reconstruction Using the Direct Frame Interpolation Method (Year: 2010).
(Continued)

*Primary Examiner* — Nizar N Sivji
(74) *Attorney, Agent, or Firm* — Bookoff McAndrews, PLLC

(57) ABSTRACT

Systems and methods for processing electronic images from a medical device comprise receiving a first image frame and a second image frame from a medical device, and determining a region of interest by subtracting the first image frame from the second image frame, the region of interest corresponding to a visual obstruction in the first image frame and/or second image frame. Image processing may be applied to the first image frame and/or second image frame based on a comparison between a first area of the first image frame corresponding to the region of interest and a second area of the second image frame corresponding to the region (Continued)

of interest, and the first image frame and/or second image frame may be provided for display to a user.

20 Claims, 6 Drawing Sheets

Related U.S. Application Data

(60) Provisional application No. 62/890,399, filed on Aug. 22, 2019.

(51) Int. Cl.
 A61B 90/00 (2016.01)
 G06T 5/00 (2024.01)
 G06T 5/30 (2006.01)

(52) U.S. Cl.
 CPC . *A61B 2090/374* (2016.02); *A61B 2090/3762* (2016.02); *A61B 2090/378* (2016.02); *G06T 2207/10016* (2013.01); *G06T 2207/10068* (2013.01); *G06T 2207/30084* (2013.01)

(58) Field of Classification Search
 CPC . G06T 5/30; G06T 2207/30084; G16H 30/40; G16H 30/20; A61B 2090/374; A61B 2090/3762; A61B 2090/378; A61B 18/26
 See application file for complete search history.

(56) References Cited

U.S. PATENT DOCUMENTS

| | | | |
|---|---|---|---|
| 2015/0283319 A1* | 10/2015 | Tolkowsky | A61B 17/3207 600/431 |
| 2017/0086795 A1* | 3/2017 | Kanayama | A61B 8/469 |
| 2017/0164844 A1* | 6/2017 | Yamada | G06T 5/50 |
| 2020/0135330 A1* | 4/2020 | Sugie | G16H 40/63 |

FOREIGN PATENT DOCUMENTS

| | | | | |
|---|---|---|---|---|
| WO | WO-2019034743 A1 * | 2/2019 | | A61B 8/08 |
| WO | WO-2019145951 A1 * | 8/2019 | | A61B 5/0084 |

OTHER PUBLICATIONS

Automatic Estimation of Coronary Blood Flow Velocity Step 1 for Developing a Tool to Diagnose Patients With Micro-Vascular Angina Pectoris (Year: 2019).

International Search Report and Written Opinion in International Application No., PCT/US2020/047338, mailed Nov. 16, 2020 (12 pages).

* cited by examiner

SYSTEMS AND METHODS FOR PROCESSING ELECTRONIC MEDICAL IMAGES TO DETERMINE ENHANCED ELECTRONIC MEDICAL IMAGES

CROSS-REFERENCE TO RELATED APPLICATION(S)

This patent application is a continuation under 37 CFR § 1.53(b) of U.S. application Ser. No. 16/999,464 filed on Aug. 21, 2020, which claims the benefit of priority from U.S. Provisional Application No. 62/890,399, filed on Aug. 22, 2019, each of which is incorporated herein by reference in its entirety.

TECHNICAL FIELD

Various aspects of the present disclosure relate generally to systems and methods useful in planning and/or performing medical procedures.

BACKGROUND

Substantial progress has been made towards increasing the effectiveness of medical treatment while reducing trauma and risks to the patient. Many procedures that once required open surgery now may be done with less invasive techniques, thus providing for less recovery time and risks of infection for the patient. Certain procedures requiring biopsy, electro-stimulation, tissue ablation, or removal of native or foreign bodies may be performed through minimally-invasive surgery.

In the field of urology, for example, renal calculi or kidney stones can accumulate in the urinary tract and become lodged in the kidney. Kidney stones are deposits of materials from the urine, typically minerals and acid salts. While smaller stones may pass from the body naturally, larger stones can require surgical intervention for removal. While open surgery was once the standard treatment for the removal of stones, other less invasive techniques, such as ureteroscopy and percutaneous nephrolithotomy/nephrolithotripsy (PCNL), have emerged as safer, effective alternatives. Additionally, advances in imaging technology have improved a medical professional's ability to identify and locate stones before and during procedures. Nevertheless, medical professionals still must analyze images to determine the location of stones and whether any stones are present. Moreover, the images are often obstructed, blurry, and/or otherwise difficult to evaluate, making the medical professional's task of discerning the presence of any stones challenging.

The systems, devices, and methods of the current disclosure may rectify some of the deficiencies described above, and/or address other aspects of the prior art.

SUMMARY

Examples of the present disclosure relate to, among other things, medical systems and methods. Each of the examples disclosed herein may include one or more of the features described in connection with any of the other disclosed examples.

In one example, the present disclosure includes a method for processing electronic images from a medical device comprise receiving a first image frame and a second image frame from a medical device, and determining a region of interest by subtracting the first image frame from the second image frame, the region of interest corresponding to a visual obstruction in the first image frame and/or second image frame. Image processing may be applied to the first image frame and/or second image frame based on a comparison between a first area of the first image frame corresponding to the region of interest and a second area of the second image frame corresponding to the region of interest, and the first image frame and/or second image frame may be provided for display to a user.

In another example, the present disclosure includes a system for processing electronic images from a medical device, the system comprising a data storage device storing instructions for processing electronic images, and a processor configured to execute the instructions to perform a method for processing electronic images. The method may comprise receiving a first image frame and a second image frame from a medical device, and determining a region of interest by subtracting the first image frame from the second image frame, the region of interest corresponding to a visual obstruction in the first image frame and/or second image frame. Image processing may be applied to the first image frame and/or second image frame based on a comparison between a first area of the first image frame corresponding to the region of interest and a second area of the second image frame corresponding to the region of interest, and the first image frame and/or second image frame may be provided for display to a user.

In another example, the present disclosure includes a non-transitory computer-readable medium storing instructions that, when executed by a computer, cause the computer to perform a method for processing electronic images from a medical device. The method may comprise receiving a first image frame and a second image frame from a medical device, and determining a region of interest by subtracting the first image frame from the second image frame, the region of interest corresponding to a visual obstruction in the first image frame and/or second image frame. Image processing may be applied to the first image frame and/or second image frame based on a comparison between a first area of the first image frame corresponding to the region of interest and a second area of the second image frame corresponding to the region of interest, and the first image frame and/or second image frame may be provided for display to a user.

BRIEF DESCRIPTION OF THE FIGURES

The accompanying drawings, which are incorporated in and constitute a part of this specification, illustrate various exemplary embodiments and together with the description, serve to explain the principles of the disclosure.

DETAILED DESCRIPTION

Examples of the present disclosure include systems and methods to facilitate, and improve the efficiency and safety of minimally-invasive surgeries. For example, aspects of the present disclosure may provide a user (e.g., a physician, medical technician, or other medical service provider) with the ability to more easily identify and, thus, remove kidney stones or other material from a patient's kidney or other organ. In some embodiments, for example, the present disclosure may be used in planning and/or performing a flexible ureteroscope procedure, with or without laser lithotripsy. Techniques discussed herein may also be applicable in other medical techniques, such as any medical technique utilizing an endoscope.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

Figure 1:
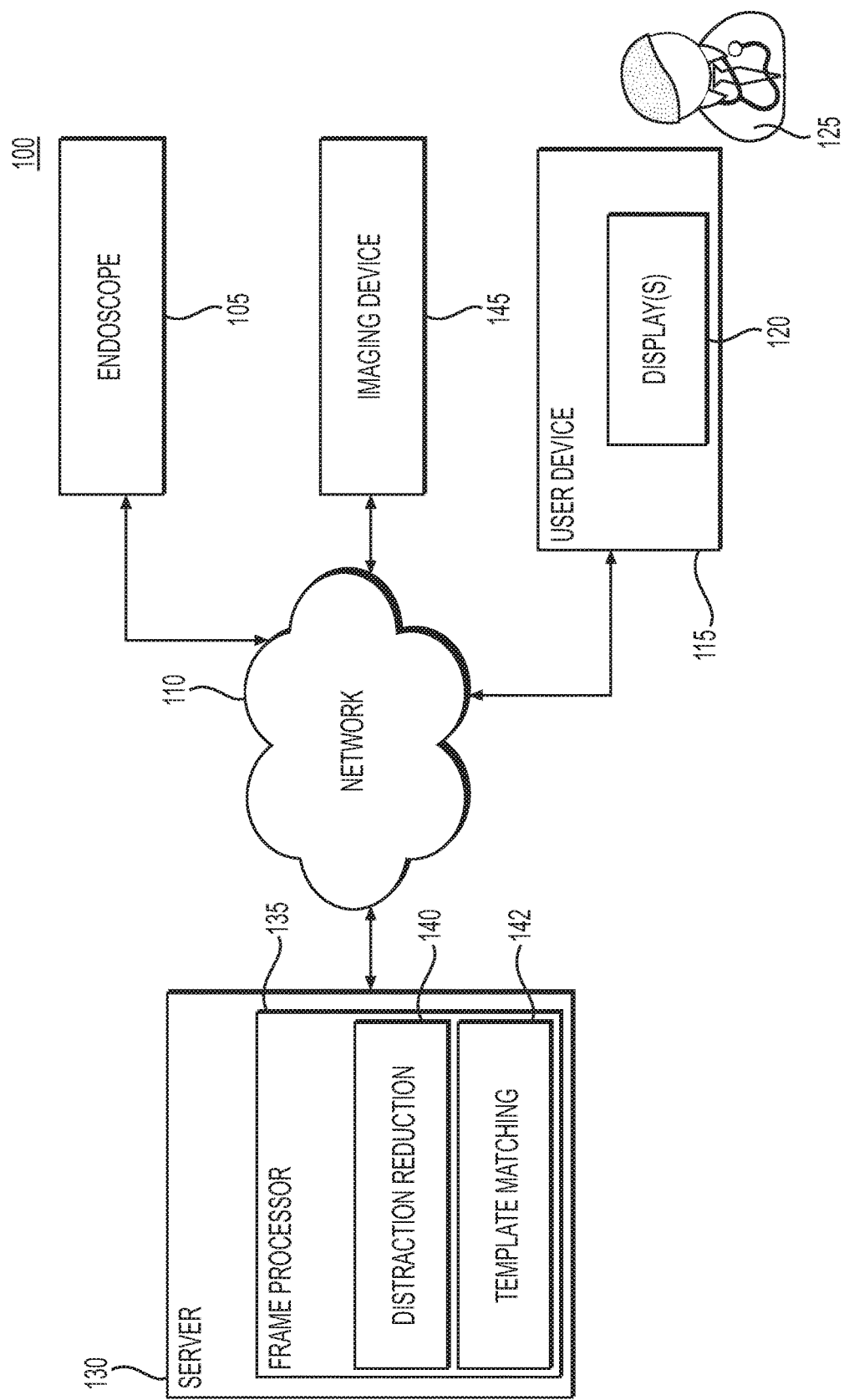
FIG. 1 illustrates a medical system, according to aspects of the present disclosure.

FIG. 1 illustrates a medical system 100 that includes a medical device such as an endoscope or other medical imaging device/medical device 105, a network 110, user device(s) 115 that may include a display(s) 120 that may be viewed by a user/practitioner/physician/patient 125, and server(s) 130 that may comprise a frame processor 135 and/or a template matcher 140. The endoscope 105, user device(s) 115, and/or server 130 may be wire connected (as shown), wirelessly connected, or otherwise communicatively coupled. Alternatively, functionality of the server 130 may be performed on endoscope 105, user device 115, etc. The server 130, endoscope 105, and/or user device 115 may further comprise a single electronic device.

As shown in FIG. 1, endoscope 105 may be an insertion device such as, for example, a ureteroscope (e.g., LithoVue™ Digital Flexible Ureteroscope by Boston Scientific Corp.).

With endoscope 105 positioned within a patient, for example, through the patient's urethra to a patient's kidney, a retrieval device (not shown) may be inserted to retrieve and remove material such as, for example, a kidney stone, with or without using laser lithotripsy. The endoscope 105 may record and/or transmit image and/or video data when inserted into a patient, and may have a light or other imaging source that may act to display images of the interior of a patient's vessels, organs, etc. The endoscope 105 may further be equipped with a laser for performance of laser lithotripsy, which may be used to remove, break up, or otherwise destroy one or more organ obstructions, such as kidney stones.

Display 120 may be a single, or at least a dual display, with either multiple screens or multiple displays on one screen. In one example, one of the displays may show an image or images currently or previously obtained by endoscope 105. The other display may show an image or video obtained from one or more additional imaging devices 145, such as by X-ray, Magnetic Resonance Imaging, Computerized Tomography Scan, rotational angiography, ultrasound, or another appropriate internal imaging device. Alternatively, one of the displays 120 may show an image modified using one or more image enhancement techniques discussed herein, while another may display an unenhanced image. Alternatively, one of the displays 120 may show an image modified using one or more enhancement techniques discussed herein, while another of the displays 120 may show an image modified using one or more different enhancement techniques discussed herein.

The software or applications, may manipulate, process, and interpret received images from imaging device 145 to identify the presence, location, and characteristics of a kidney stone or other material. As will be discussed further herein, the frame processor 135 and/or template matching applications 140 may process and enhance received images from endoscope 105.

The physician may insert endoscope 105 into a patient when performing a medical procedure such as a lithotripsy to remove a kidney stone. The display 120 may become partially or completely obscured by pieces of kidney stone or other floating particulate matter, for example, when illuminated by a light on the endoscope 105. Additionally, a flash created by a laser or other light source emitted from the endoscope 105 may cause surgeons or technicians to lose track of the kidney stone or other object of the medical procedure. The difficulty in tracking the kidney stone or object of the procedure may increase the time of performing the medical procedure, may increase the rate of errors of the medical procedure, and may increase the cognitive load in maintaining visual track of the object.

Figure 2:
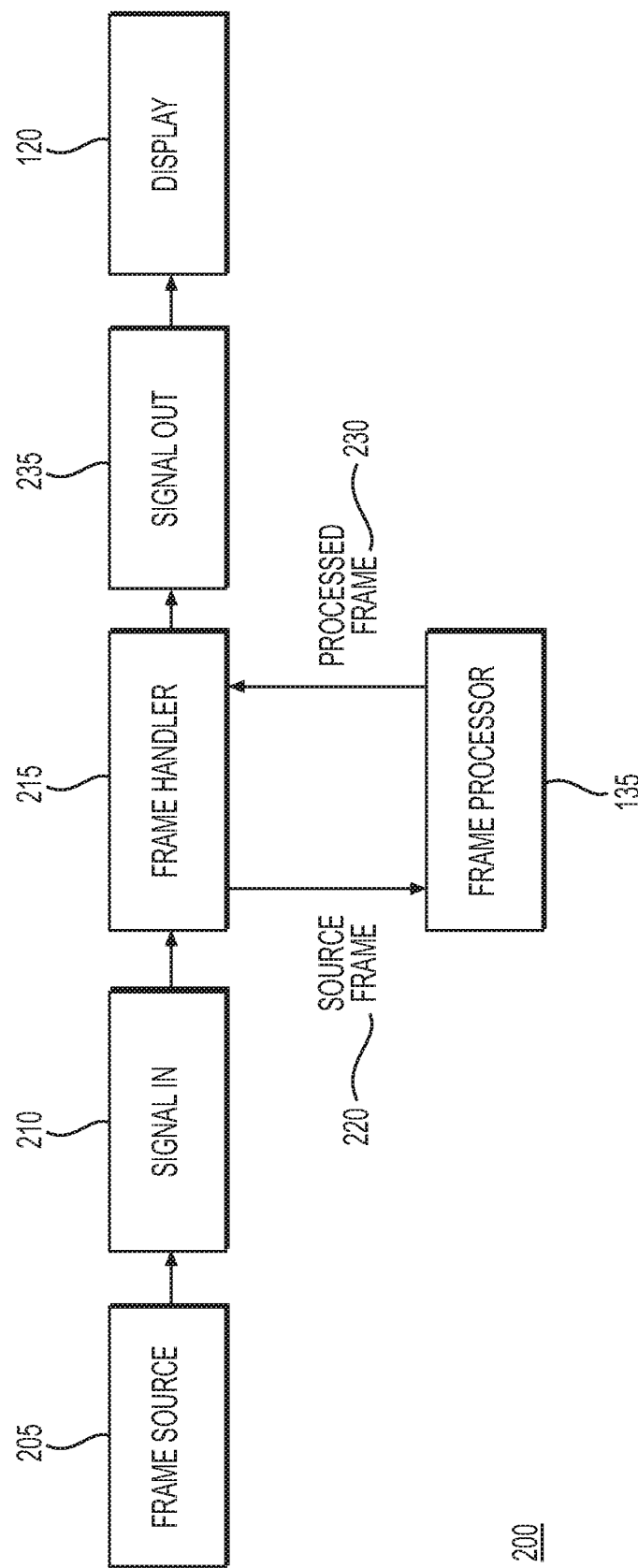
FIG. 2 is a flow diagram of an exemplary method for processing medical images, according to aspects of the present disclosure.

FIG. 2 is a flow diagram of an exemplary method for processing medical images, according to aspects of the present disclosure. A source of video or image frames 205, which may be any medical device, such as an endoscope 105 or imaging device 145, may provide frames to signal in 210. The frames may be provided to a frame handler 215, which may store a plurality of frames. One or more frames 220 may be provided to a frame processor 135, which may produce one or more processed frames 230. The processed frames 230 may be provided to the signal out 235, which may be shown on display 120.

The signal in 210 may be a software handler that may transmit that a new frame has been received. The frame handler 215 may either directly send a frame via the signal out 235 to a display 120, or it may send one or more frames to the frame processor 135. As will be discussed elsewhere herein, the frame processor 135 may perform distraction reduction and/or template matching techniques. The frame handler 215 may also send the original frame to the display 120, and also send a copy of the frame to the frame processor 135. The processed frame 230 may be received and also forwarded to the display 120. This may allow for the original frame to be displayed alongside the processed frame 230 at the display 120. Alternatively, the frame handler 215 may send the source frame 220 to the frame processor 135, and the frame processor may return a processed frame 230 that comprises a dual display of the original and enhanced frame. Accordingly, the processed frame 230 may be larger than the source frame. The frame processor 135 may further add buttons or other user interface elements to the processed frame 230.

Although techniques discussed herein are discussed as happening on the frame processor 135, which may be depicted as being located on a single device, any of the functions of the frame processor may be spread across any number of devices, for example, any of the devices depicted in system 100. Further, one or more of the signal in 210, frame handler 215, and/or signal out 235 may be housed on one or more servers 130, or any of the other devices pictured on system 100.

Figure 3:
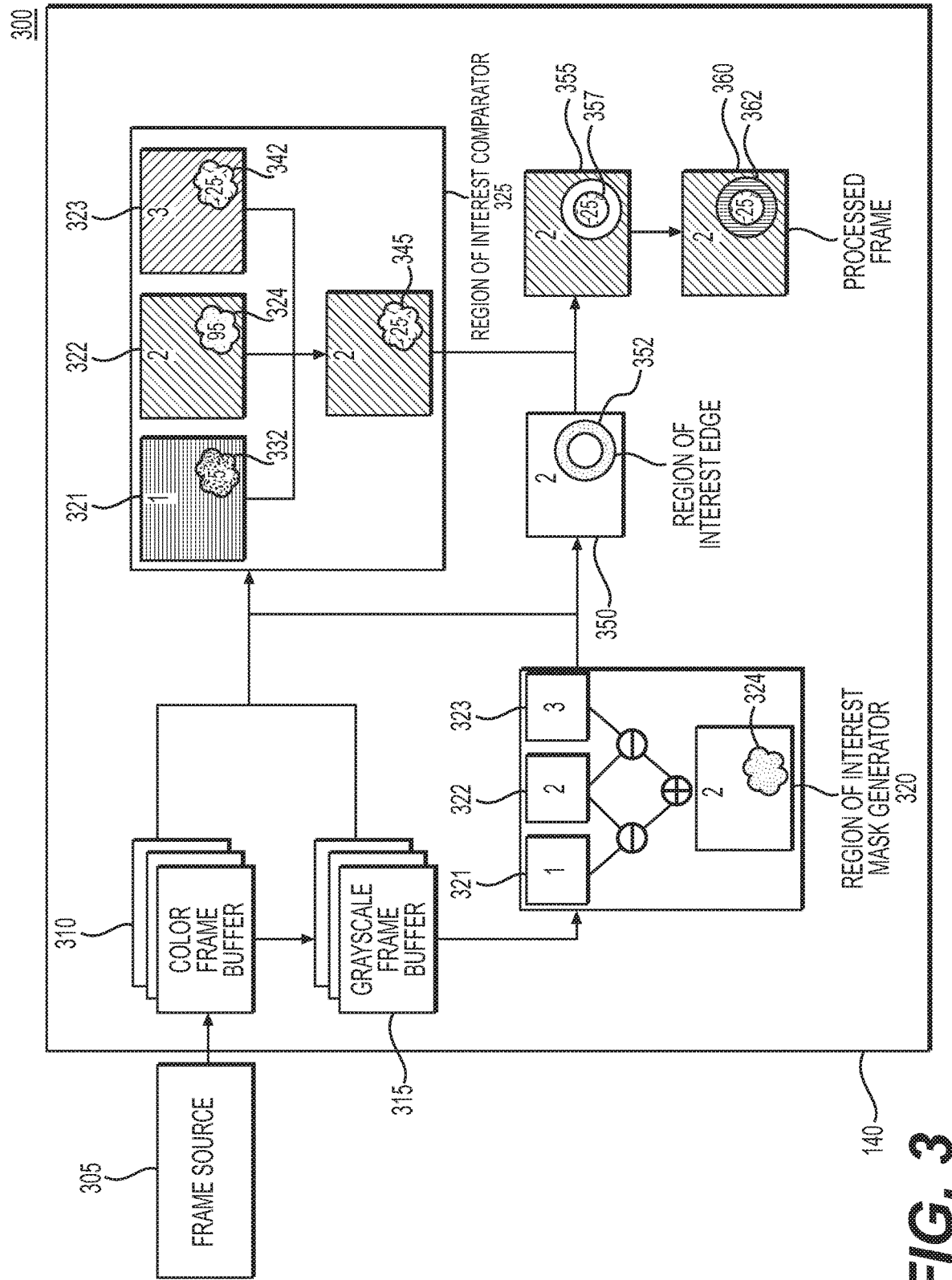
FIG. 3 is a flow diagram of an exemplary method for determining a region of interest in medical images, according to aspects of the present disclosure.

FIG. 3 is a flow diagram of an exemplary method for distraction deduction, according to aspects of the present disclosure. A plurality of frames may be received from a frame source 305. The frame source may comprise an endoscope 105 or other medical imaging device 145. One or more frames may be accumulated at a color frame buffer 310 and/or a grayscale frame buffer 315. A plurality of frames may be accumulated for comparison. By comparing multiple frames with each other, a background may be discerned and distinguished from a visual obstruction. The visual obstruction may be a reflection, glare, light source, piece of dust, debris, particle, piece of kidney or gall stone or other calculus, etc. The visual obstruction may also have an associated brightness or intensity that is beyond a threshold. Using techniques discussed herein, the visual obstruction may be identified as a region of interest, and may receive processing to remove or mitigate the extent or severity of the obstruction.

When a new frame is received from the frame source 305, a copy may be stored in the color frame buffer 310 and/or the grayscale frame buffer 315. Frames in the color frame buffer 310 may have a plurality of channels for a plurality of colors, for example, three channels for red, green and blue. A copy of the frame may be stored in grayscale frame buffer 315. The grayscale frame buffer 315 and/or the color frame buffer 310 may be used to determine one or more regions of interest in the frame, which may comprise one or more visual obstructions.

A received color frame may be converted to grayscale for storage in the grayscale frame buffer 315. Conversion may comprise combining two or more of the color channels to form a grayscale frame. This may be done, at least in part, because different color channels in color frames may disagree about whether there is a visual obstruction (e.g., light intensity beyond a threshold, piece of debris beyond a size threshold, etc.). A combined-channel frame might not have such disagreements, since there is only one channel, yet the information from the multiple channels may still be present in the combined-channel frame.

Alternatively, a region of interest may be identified without determining grayscale frames. Any color channel which reports a visual obstruction according to techniques discussed herein may be used to determine a region of interest, even if there is disagreement from other color channels about whether there is any region of interest.

The region of interest mask generator 320 may receive frames from the grayscale frame buffer 315 and/or the color frame buffer 310. The region of interest mask generator 320 may determine areas (regions of interest) with intensity changes that may be removed from the presented frame. A plurality of received frames, which may be consecutive frames, may be compared, and the common features may be subtracted. For example, if a current frame 322 is being processed to determine a region of interest, it may be compared with preceding frame 321 and the subsequent/later frame 323. Common features, or features that are determined to be similar within a predetermined threshold, of the frames may be subtracted from each other. Two processed frames may be generated, the first a subtraction of the prior frame 321 and the current frame 322, and the second a subtraction of the subsequent frame 323 and the current frame 322. The two processed frames may then be added to each other. Any objects remaining may be designated as region(s) of interest 324.

The common features may be the background, and thus, after the subtraction, only objects moving more quickly than the background, such as pieces of debris and other visual obstructions, may remain. These one or more visual obstructions may be designated as a region of interest and a region of interest mask may be applied.

Visual obstructions may also be objects with a light intensity that is beyond a threshold. For example, a reflection of a light or laser beyond a brightness/intensity threshold may not come from a particle or other object moving near the endoscope, but rather may come from light reflecting off the kidney stone itself, vessel/tissue/organ wall, or some other object that may not subtract out from nearby frames. Thus, regions of interest may also or alternatively be designated for any region with a light intensity/brightness exceeding a predetermined threshold. By comparing nearby frames, before and/or after the frame receiving processing, this type of visual obstruction may be identified. For example, a current frame 322 may be the frame receiving processing. The current frame 322 may be compared to a frame prior in time 321 that did not have the intense light visual obstruction. The two frames may be subtracted to determine a first subtracted frame. The current frame 323 may then be compared to a frame afterwards in time 323 that did not have intense light visual obstruction. The two frames may be subtracted to determine a second subtracted frame. The two subtracted frames may then be added together to determine the region of interest mask. This process may be repeated with more frames from which subtractions are performed. Alternatively, the determination of the region of interest may be performed by only comparing the frame to be processed to one other frame.

The one or more frames may be provided with the identified one or more regions or interest 324 to the region of interest comparator 325. Now that the region(s) of interest is determined, it may be analyzed relative to one or more color channels of the associated color version of the frame. At a first color channel, for example red, two or more frames may be analyzed. For example, the frame being processed 322 may be compared with prior frame 321 and subsequent frame 323. Image characteristics may be compared of the determined regions of interest 324 across a plurality of respective frames. For example, image characteristics the region of interest 324 of the current frame 322 may be compared to the corresponding region of interest 332 of prior frame 321. The region of interest 332 may cover the same area of the frame as the region of interest 324. Image characteristics of the region of interest 324 of the current frame 322 may further be compared to the region of interest 342 of subsequent frame 323. For example, the image characteristics compared may be brightness, intensity, amount of intensity change relative to other frames, deviation from average brightness across a predetermined number of frames, motion pattern, texture, intensity histogram, entropy, etc.

In one embodiment, the intensity of a color channel across multiple frames may be compared, and the lowest, median, or average intensity may be determined. For example, in the red channel, pixels, on average, in region of interest 332 may have an intensity of 5, while region of interest 324 may have an intensity of 95, and region of interest 342 may have an intensity of 25. The plurality of frames may have a visual obstruction that is very dark or very bright. Accordingly, the median value of the intensity across multiple frames may be selected. The pixels of the region of interest with the median value may be made to replace the pixels of the region of interest of the current frame 322. This determination may be made for the other color channels, for example green and blue. It is possible that the regions of interest on some color channels will be replaced with that of another frame, while the regions of interest on other color channels will remain uncorrected. The color channels may be processed in this manner until all channels have a processed region of interest, as necessary. In the example of FIG. 3, region of interest 342 of subsequent frame 323 may replace the region of interest 324 of the current frame 322, as shown in FIG. 3 as region of interest 345. In this manner, a bright flash or dark obstruction in the current frame may be replaced to mitigate or eliminate the visual obstruction.

A possible side effect of replacing regions of interest, as described above, is that hard or artificial edges (halos) may appear around the replaced regions. This may distort the viewer's perception of the true shape of the object receiving image correction, and may give the viewer the impression of edges that are not actually present in the body of the patient.

To mitigate or eliminate this problem, after the region of interest is determined, at 350 an edge 352 of the region of interest may be determined. This edge 352 may be of a predetermined thickness, or may be based on the dimensions of the region of interest. For example, as the region of interest gets larger, the edge 352 may automatically be determined to be thicker. The edges may be determined using morphological operations (for example, dilation and erosion operations). The region of interest edge may be placed over the current frame 355 with the replaced region of interest 357. The edge of the replaced region of interest 357 may be removed. The region of interest edge may be in-painted, or may have a color gradient from the inside edge to the outside edge applied such that the "halo" of the processed current frame is removed/smoothed out, and any harsh edges that may cause visual distraction are removed. The color gradient might not only be a first-degree gradient, but also a second derivative gradient to help smooth the color transition from the inside to the outside of the edge 352. After these techniques are applied, a processed frame 360, with corrected edge 362, may be provided for display to a user.

Figure 4:
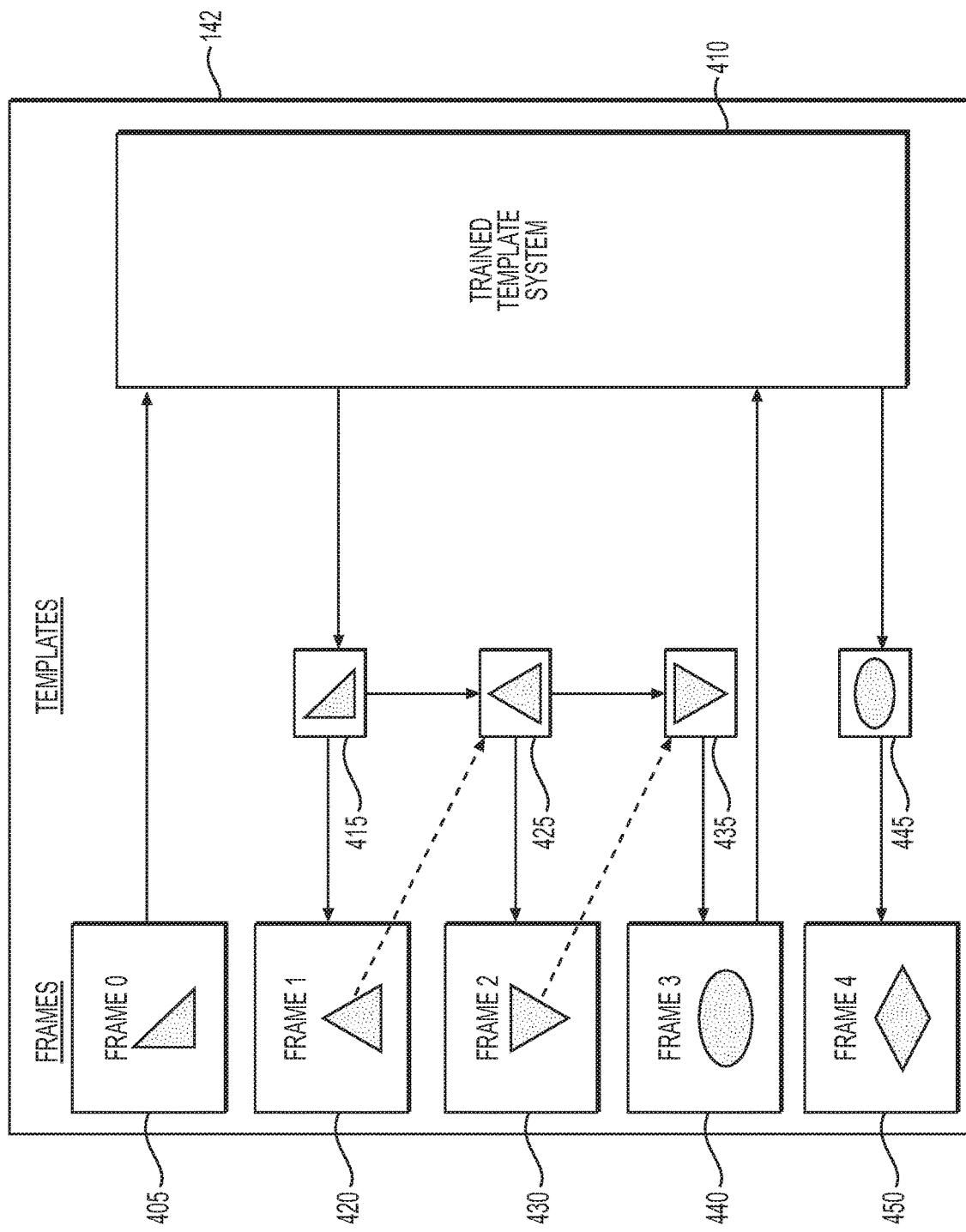
FIG. 4 is a flow diagram of an exemplary method for determining a template for object tracking in medical images, according to aspects of the present disclosure.

FIG. 4 is a flow diagram of an exemplary method for determining a template for object tracking in medical images, according to aspects of the present disclosure. As discussed above, it may be difficult for an endoscope operator to track a target object or tissue, such as a kidney stone. In addition to visual obstructions, there is movement of the endoscope and other effects that may increase the tracking difficulty and thereby the cognitive load of the endoscope operator. While processing frames to reduce or remove visual obstructions may make the process easier, it may help to highlight or otherwise indicate the target tissue or object on the display automatically. For example, a box or outline may be placed around the target object, such as a kidney stone. FIG. 4 discloses techniques of template matching 142, which may be performed separately from, or in addition to, distraction deduction techniques discussed elsewhere herein.

At frame 0 (405), the frame may be provided to a trained template system 410. The trained template system 410 may have been trained with images of the target object, such as images of kidney stones. The trained template system may return a portion of frame 0 corresponding to the target object, for example, the portion of frame 0 containing an image of the kidney stone, indicated as template 415. Template 415 may be used to quickly and automatically identify the same target object in subsequent frame 1 (420). For the given template and target frame, various image features may be determined (intensity, gradient, etc.) for both, which may be used to determine if a match exists. The target object in frame 1 may be somewhat different, as it may have rotated, changed shape (been fragmented), move closer or further from the camera, etc. That said, if template 415 matches any region of frame 1 within a predetermined tolerance/confidence threshold, the matching region may be assumed to be the target object in the subsequent frame. In this manner, using templates taken from prior frames, an object may be tracked across a plurality of frames. As discussed above, a bounding box, a circle, pointer, or any other indicator may be placed around the target object to allow for easier user tracking of the object. In addition, an indicator of the confidence of the match may also be determined and/or displayed.

A portion of frame 1 may be used to generate template 425. Template 425 may be used to locate the target object in subsequent frame 2 (430). The portion of frame 2 containing the target object may be used to generate template 435. Using templates may be faster and computationally less intensive than providing each frame to the trained template system 410 for tracking the target object. Accordingly, templates might be used preferentially, unless the target object cannot be tracked within a predetermined confidence. Template 435 may be used to recognize the target object in frame 3 (440).

The templates may be compared rapidly against each portion of the frame to determine if there is a match within a predetermined threshold or confidence. However, there might not be a match to within a predetermined threshold or confidence. For example, a kidney stone may be fragmented and be shaped substantially differently from one frame to the next. If, for example, the target object is not recognizable within a tolerance using a template from the prior frame, the frame, such as a frame 3, may be provided again to the trained template system 410. The trained template system 410 may return template 445, which may be used to recognize the target object in frame 4 (450), and so on.

In addition, a buffer of templates may be stored from prior frames. If an object occludes the endoscope 105 or other medical imaging device, if only templates of the immediately prior frame were used to track the target object, tracking of the target object might quickly fail. In the event that the target object is not recognized within a predetermined confidence, additional prior templates may be analyzed to search for a match.

Figure 5:
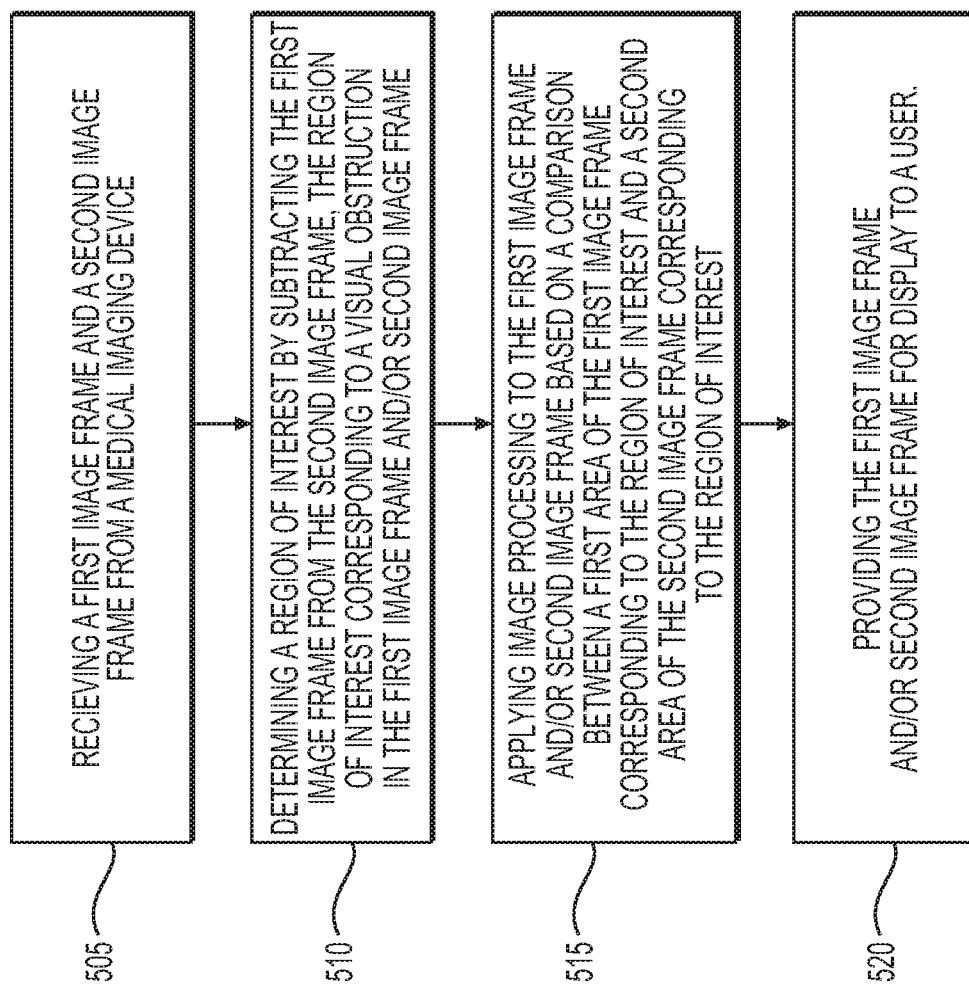
FIG. 5 is a flow diagram of an exemplary method for determining medical image enhancement, according to aspects of the present disclosure.

FIG. 5 is a flow diagram of an exemplary method for determining medical image enhancement, according to aspects of the present disclosure. At step 505, a first image frame and a second image frame may be received from a medical imaging device. At step 510, a region of interest may be determined by subtracting the first image frame from the second image frame, the region of interest corresponding to a visual obstruction in the first image frame and/or second image frame. At step 515, image processing may be applied to the first image frame and/or second image frame based on a comparison between a first area of the first image frame corresponding to the region of interest and a second area of the second image frame corresponding to the region of interest. At step 520, the first image frame and/or second image frame may be provided for display to a user.

Figure 6:
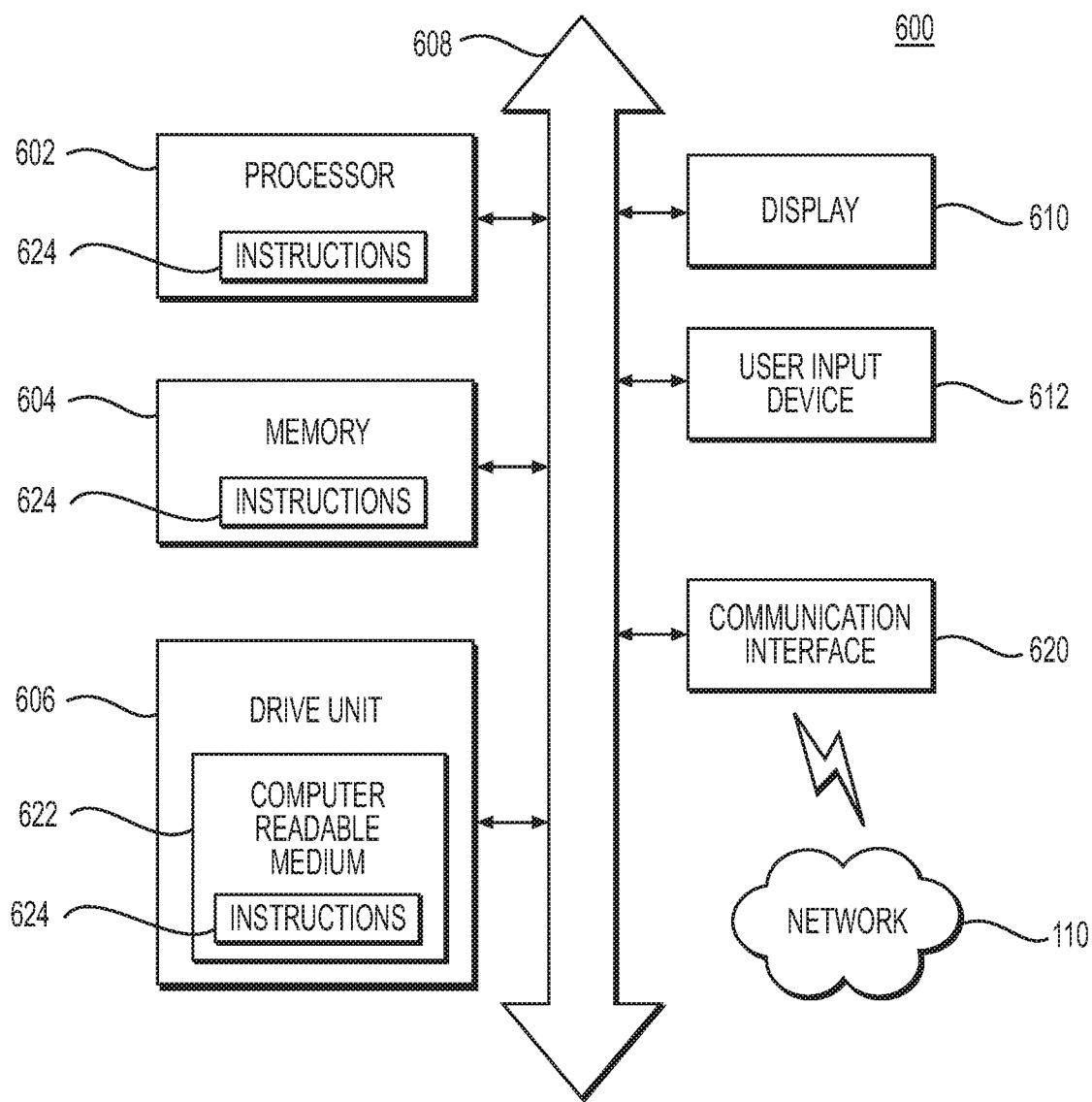
FIG. 6 illustrates an exemplary system that may be used in accordance with techniques discussed in FIGS. 1-5, according to aspects of the present disclosure.

FIG. 6 illustrates an exemplary system that may be used in accordance with techniques discussed in FIGS. 1-5, according to aspects of the present disclosure. FIG. 6 is a simplified functional block diagram of a computer that may be configured as server 130, endoscope 105, imaging device 145, and/or user device 115, according to exemplary embodiments of the present disclosure. Specifically, in one embodiment, any of the user devices, servers, etc., discussed herein may be an assembly of hardware 600 including, for example, a data communication interface 620 for packet data communication. The platform also may include a central processing unit ("CPU") 602, in the form of one or more processors, for executing program instructions. The platform may include an internal communication bus 608, and a storage unit 606 (such as ROM, HDD, SDD, etc.) that may store data on a computer readable medium 622, although the system 600 may receive programming and data via network communications. The system 600 may also have a memory 604 (such as RAM) storing instructions 624 for executing techniques presented herein, although the instructions 624 may be stored temporarily or permanently within other modules of system 600 (e.g., processor 602 and/or computer readable medium 622). The system 600 also may include input and output ports 612 and/or a display 610 to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

The disclosed techniques may help enable efficient and effective procedures to breakup and/or remove material from a patient's organ. In particular, the user may easily view the processed frames to assist with, for example, removing kidney stones within the patient's kidney. The image may be clearer, with less visual obstructions, and the target kidney stone may be easier to track due to an indicator following its location. Therefore, in the kidney stone example, the user may more efficiently remove the kidney stones from specific locations within the patient's kidney.

Moreover, while examples discussed in this disclosure are commonly directed to ureteroscopic kidney stone removal, with or without lithotripsy, it is further contemplated that the systems and procedures discussed herein may be equally applicable to other material removal procedures. For example, the systems and methods discussed above may be used during a percutaneous nephrolithotomy/nephrolithotripsy (PCNL) to plan for a procedure and mid-procedure to locate any missed kidney stones. The systems and methods discussed above may also be used to plan for or conduct procedures to remove ureteral stones, gallstones, bile duct stones, etc.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A method for processing electronic images from a medical device, comprising:
   receiving a first image frame and a second image frame from a medical device;
   determining a region of interest by subtracting the first image frame from the second image frame, wherein a first area of the first image frame and a second area of the second image frame correspond to the region of interest, and the second area of the second image frame includes a visual obstruction, the visual obstruction including a reflection and/or a glare;
   receiving a third image frame from the medical device, wherein a third area of the third image frame corresponds to the region of interest;
   comparing image characteristics across the first area of the first image frame, the second area of the second image frame, and the third area of the third image frame corresponding to the region of interest; and
   applying image processing to the second area of the second image frame corresponding to the region of interest, based on the comparison of the image characteristics, to mitigate or eliminate the visual obstruction, the image processing including a replacement of the second area of the second image frame with one of the first area of the first image frame or the third area of the third image frame determined based on the comparison of the image characteristics.

2. The method of claim 1, wherein the image characteristics include brightness, intensity, amount of intensity change relative to other image frames, and/or deviation from average brightness across the first area of the first image frame, the second area of the second image frame, and the third area of the third image frame.

3. The method of claim 1, wherein subtracting the first image frame from the second image frame comprises removing regions from consideration for the region of interest if the regions are similar beyond a predetermined threshold in both the first image frame and the second image frame.

4. The method of claim 1, further comprising:
   generating a grayscale first image frame based on the first image frame;
   generating a grayscale second image frame based on the second image frame; and
   determining the region of interest based on the grayscale first image frame and the grayscale second image frame.

5. The method of claim 1, wherein determining the region of interest further comprises:
   subtracting the first image frame from the second image frame to form a first subtracted image frame;
   subtracting the second image frame from the third image frame to form a second subtracted image frame; and
   adding the first subtracted image frame and the second subtracted image frame.

6. The method of claim 1, wherein comparing the image characteristics comprises:
    determining a first pixel value associated with the first area of the first image frame corresponding to the region of interest;
    determining a second pixel value associated with the second area of the second image frame corresponding to the region of interest;
    determining a third pixel value associated with the third area of the third image frame; and
    comparing the first pixel value, the second pixel value, and the third pixel value.

7. The method of claim 6, wherein applying the image processing to the second area of the second image frame further comprises:
    determining a median pixel based on the comparing of the first pixel value, the second pixel value, and the third pixel value;
    upon determining that the first pixel value is the median pixel, replacing the second area of the second image frame corresponding to the region of interest with the first area of the first image frame corresponding to the region of interest; and
    upon determining that the third pixel value is the median pixel, replacing the second area of the second image frame corresponding to the region of interest with the third area of the third image frame corresponding to the region of interest.

8. The method of claim 7, wherein the steps of determining the median pixel and replacing the second area of the second image frame are performed one color channel at a time.

9. The method of claim 1, further comprising:
    determining a border of a predetermined thickness around the second area of the second image frame corresponding to the region of interest; and
    applying a color gradient across the border.

10. The method of claim 1, further comprising:
    determining a first template associated with an object of interest in the first image frame, the first template comprising a portion of the first image frame depicting the object of interest; and
    determining a location of the object of interest in the second image frame based on the first template.

11. The method of claim 10, wherein determining the location of the object of interest in the second image frame further comprises:
    comparing the first template with a plurality of regions of the second image frame; and
    upon locating a region of the second image frame that matches the first template within a predetermined tolerance, associating the region of the second image frame with the object of interest.

12. The method of claim 10, further comprising:
    providing an indication of the region of the second image frame with the object of interest for display.

13. A system for processing electronic images from a medical device, comprising:
    a data storage device storing instructions for processing electronic images; and
    a processor configured to execute the instructions to perform a method for processing electronic images, the method including:
        receiving a first image frame, a second image frame, and a third image frame from a medical device;
        determining a region of interest by subtracting at least one of the first image frame or the third image frame from the second image frame, wherein a first area of the first image frame, a second area of the second image frame, and a third area of the third image frame correspond to the region of interest, and the second area of the second image frame includes a visual obstruction, the visual obstruction including a reflection and/or a glare;
        comparing image characteristics across the first area of the first image frame, the second area of the second image frame, and the third area of the third image frame corresponding to the region of interest; and
        applying image processing to the second area of the second image frame corresponding to the region of interest, based on the comparison of the image characteristics, to mitigate or eliminate the visual obstruction, the image processing including a replacement of the second area of the second image frame with one of the first area of the first image frame or the third area of the third image frame determined based on the comparison of the image characteristics.

14. The system of claim 13, wherein subtracting at least one of the first image frame or the third image frame from the second image frame comprises removing regions from consideration for the region of interest if the regions are similar beyond a predetermined threshold in both the first image frame and the second image frame or in both the third image frame and the second image frame.

15. The system of claim 13, the method executed by the system further comprising:
    generating a grayscale first image frame based on the first image frame;
    generating a grayscale second image frame based on the second image frame;
    generating a grayscale third image frame based on the third image frame; and
    determining the region of interest by subtracting at least one of the grayscale first image frame or the grayscale third image frame from the grayscale second image frame.

16. The system of claim 13, wherein determining the region of interest further comprises:
    subtracting the first image frame from the second image frame to form a first subtracted image frame;
    subtracting the second image frame from the third image frame to form a second subtracted image frame; and
    adding the first subtracted image frame and the second subtracted image frame.

17. The system of claim 13, wherein applying the image processing to the second area of the second image frame comprises:
    determining a first pixel value associated with the first area of the first image frame corresponding to the region of interest;
    determining a second pixel value associated with the second area of the second image frame corresponding to the region of interest;
    determining a third pixel value associated with the third area of the third image frame;
    determining a median pixel by comparing the first pixel value, the second pixel value, and the third pixel value;
    upon determining that the first pixel value is the median pixel, replacing the second area of the second image frame corresponding to the region of interest with the first area of the first image frame corresponding to the region of interest; and
    upon determining that the third pixel value is the median pixel, replacing the second area of the second image frame corresponding to the region of interest with the third area of the third image frame corresponding to the region of interest.

18. The system of claim 17, wherein the steps of determining the median pixel and replacing the second area of the second image frame are performed one color channel at a time.

19. A non-transitory computer-readable medium storing instructions that, when executed by a computer, cause the computer to perform a method for processing electronic images from a medical device, the method including:
   receiving a first image frame, a second image frame, and a third image frame from the medical device;
   determining a region of interest by subtracting at least one of the first image frame or the third image frame from the second image frame, wherein a first area of the first image frame, a second area of the second image frame, and a third area of the third image frame correspond to the region of interest, and the second area of the second image frame includes a visual obstruction, the visual obstruction including a reflection and/or a glare;
   comparing image characteristics across the first area of the first image frame, the second area of the second image frame, and the third area of the third image frame corresponding to the region of interest;
   determining one of the first area of the first image frame or the third area of the third image frame to replace the second area of the second image frame based on the comparison of the image characteristics; and
   applying image processing to the second area of the second image frame corresponding to the region of interest, based on the comparison of the image characteristics, to mitigate or eliminate the visual obstruction, the image processing including a replacement of the second area of the second image frame with the determined one of the first area of the first image frame or the third area of the third image frame.

20. The system of claim 13, wherein the image characteristics include intensity values of first pixels comprising the first area of the first image frame, second pixels comprising the second area of the second image frame, and third pixels comprising the third area of the third image frame, and wherein comparing the image characteristics comprises:
   determining the one of the first area of the first image frame or the third area of the third image frame to replace the second area of the second image frame based on a comparison of the intensity values of the first pixels, second pixels, and third pixels.

* * * * *